US007772003B2

(12) United States Patent
Lehn et al.

(10) Patent No.: US 7,772,003 B2
(45) Date of Patent: Aug. 10, 2010

(54) LIPID DERIVATIVES OF AMINOGLYCOSIDES

(75) Inventors: Jean-Marie Lehn, Strasbourg (FR); Pierre Lehn, Paris (FR); Jean-Pierre Vigneron, Boissy-sur-Saint-Yon (FR)

(73) Assignees: Aventis Pharma S.A. (FR); Centre National de la Recherche Scientifique (CNRS) (FR); Institut Nationale de la Sante et de la Recherche Medicale (INSERM) (FR)

( * ) Notice: Subject to any disclaimer, the term of this patent is extended or adjusted under 35 U.S.C. 154(b) by 899 days.

(21) Appl. No.: 10/228,959

(22) Filed: Aug. 28, 2002

(65) Prior Publication Data

US 2003/0054556 A1    Mar. 20, 2003

Related U.S. Application Data

(60) Provisional application No. 60/331,452, filed on Nov. 16, 2001.

(30) Foreign Application Priority Data

Aug. 29, 2001   (FR) .................................. 01 11199

(51) Int. Cl.
*C12N 15/88* (2006.01)
*C12N 15/00* (2006.01)
*C12N 5/00* (2006.01)
*A61K 9/127* (2006.01)
*A61K 31/70* (2006.01)

(52) U.S. Cl. .................. 435/458; 435/325; 435/375; 435/455; 424/450; 514/44 R

(58) Field of Classification Search ............ 435/6, 435/325, 375; 514/44; 424/450
See application file for complete search history.

(56) References Cited

U.S. PATENT DOCUMENTS

| 3,293,128 | A | * | 12/1966 | Mann ............................ 514/36 |
| 4,400,375 | A | * | 8/1983 | Douthart et al. ................ 514/34 |
| 5,744,133 | A | | 4/1998 | Lathe et al. |
| 5,789,245 | A | * | 8/1998 | Dubensky et al. ......... 435/320.1 |
| 5,866,551 | A | | 2/1999 | Benoit et al. |
| 5,945,400 | A | | 8/1999 | Scherman et al. |
| 5,965,519 | A | * | 10/1999 | Yatvin et al. .................... 514/2 |
| 6,143,729 | A | | 11/2000 | Lehn et al. |
| 6,153,597 | A | | 11/2000 | Blanche et al. |
| 6,171,612 | B1 | * | 1/2001 | Byk et al. .................... 424/450 |
| 6,200,956 | B1 | | 3/2001 | Scherman et al. |
| 6,410,049 | B1 | * | 6/2002 | Papahadjopoulos et al. . 424/450 |
| 6,426,216 | B1 | | 7/2002 | Perricaudet et al. |
| 2002/0031499 | A1 | | 3/2002 | Haddada et al. |
| 2002/0058795 | A1 | * | 5/2002 | Mumper et al. ............... 536/7.2 |
| 2002/0122789 | A1 | | 9/2002 | Perricaudet et al. |

FOREIGN PATENT DOCUMENTS

| EP | 0 185 573 | | 6/1986 |
| EP | 0 259 212 | | 3/1988 |
| EP | 0 321 201 | | 6/1989 |
| EP | 0 140 308 | | 5/1995 |
| EP | 0 888 379 | | 1/1999 |
| FR | 91/11947 | | 4/1993 |
| FR | 93/04745 | | 10/1994 |
| GB | 1332812 | A | * 10/1973 |
| WO | WO 96/25508 | | 8/1996 |
| WO | WO 97/12051 | | 4/1997 |
| WO | WO 97/18185 | | 5/1997 |
| WO | WO 9718185 | A1 | * 5/1997 |
| WO | WO 9855490 | A1 | * 12/1998 |
| WO | WO 0039139 | A1 | * 7/2000 |
| WO | WO 0040692 | A2 | * 7/2000 |

OTHER PUBLICATIONS

English Translation of WO9855490.*
Douthart et al. Journal of Interferon Research, vol. 2, No. 4, 1982, pp. 493-499.*
Belmont, Philippe et al., "Aminoglycoside—derived cationic lipids as efficient vectors for gene transfection in vitro and in vivo," The Journal of Gene Medicine, 4:517-526 (2002).
Sainlos, Matthieu et al., Kanamycin A—derived cationic lipids as vectors for gene transfection, ChemBioChem, 6:1023-1033 (2005).
Sainlos, Matthieu, Abstract of doctoral thesis, Ecole doctorale de chimie moléculaire de Paris centre, Université Pierre et Marie Curie (Paris VI), Jul. 6, 2004.
Bessodes, et al., "Synthesis and Biological Properties of New Glycosidic Cationic Lipids for DNA Delivery," Bioorganic & Medicinal Chem. Lett. 10 (2000), pp. 1393-1395.
C. Jacopin et al., "Synthesis and Transfecting Properties of a Glycosylated Polycationic DNA Vector," Bioorganic & Medicinal Chem. Lett. 11 (2001), pp. 419-422.
Walter, et al., Aminoglycoside-RNA interactions, Current Opinion Chemical Biology (1999), pp. 694-704.
Moazed et al., Interaction of antibiotics with functional sites in 16S ribosomal RNA, Nature (1987), vol. 327, pp. 389-394.
Purohit, et al., "Interactions of a small RNA with antibiotic and RNA ligands of the 30S subunit," Nature (1994), vol. 370, pp. 659-662.
Baker, et al., "Synthesis and Anti-HIV Activity of Guanidinoglycosides," J. Org. Chem. (2000), pp. 9054-9058.
Luedtke, et al., "Guanidinoglycosides: A Novel Family of RNA Ligands," J. Am. Chem. Soc. (2000), 122, pp. 12035-12036.
Iwanowicz, et al., "Preparation of N,N'-Bis-*tert*-Butoxycarbonylthiourea," Synthetic Communications, (1993), pp. 1443-1445.
Felgner, et al., "Artificial Self-Assembling Systems for Gene Delivery," (1996), pp. 176-190, Conference Proceedings Series, American Chemical Society, Wash. DC.
Ferrari, Marilyn E., et al., "Trends in lipoplex physical properties dependent on cationic lipid structure, vehicle and complexation procedures do not correlate with biological activity," Nucleic Acids Research 29(7):1539-1548 (2001).
Simberg, Dmitri et al., "Phase behavior, DNA ordering, and size instability of cationic lipoplexes," Journal of Biological Chemistry, 276(50):47453-47459 (2001).
Zuhorn, Inge S., et al., "Phase behavior of cationic amphiphiles and their mixtures with helper lipid influences lipoplex shape, DNA translocation, and transfection efficiency," Biophysical Journal, 83:2096-2108 (2002).

* cited by examiner

*Primary Examiner*—Janet Epps-Smith
(74) *Attorney, Agent, or Firm*—Finnegan, Henderson, Farabow, Garrett & Dunner, LLP

(57) ABSTRACT

Transfecting compounds which include an aminoglycoside linked to a lipid via a spacer, and their polyguanidylated derivatives are provided. These compounds are useful for the in vitro, ex vivo, or in vivo transfection of nucleic acids into various cell types.

31 Claims, 12 Drawing Sheets

KanaChol/DNA formulations at various charge ratios

KanaChol/DOPE/DNA formulations at various charge ratios

Figure 1:
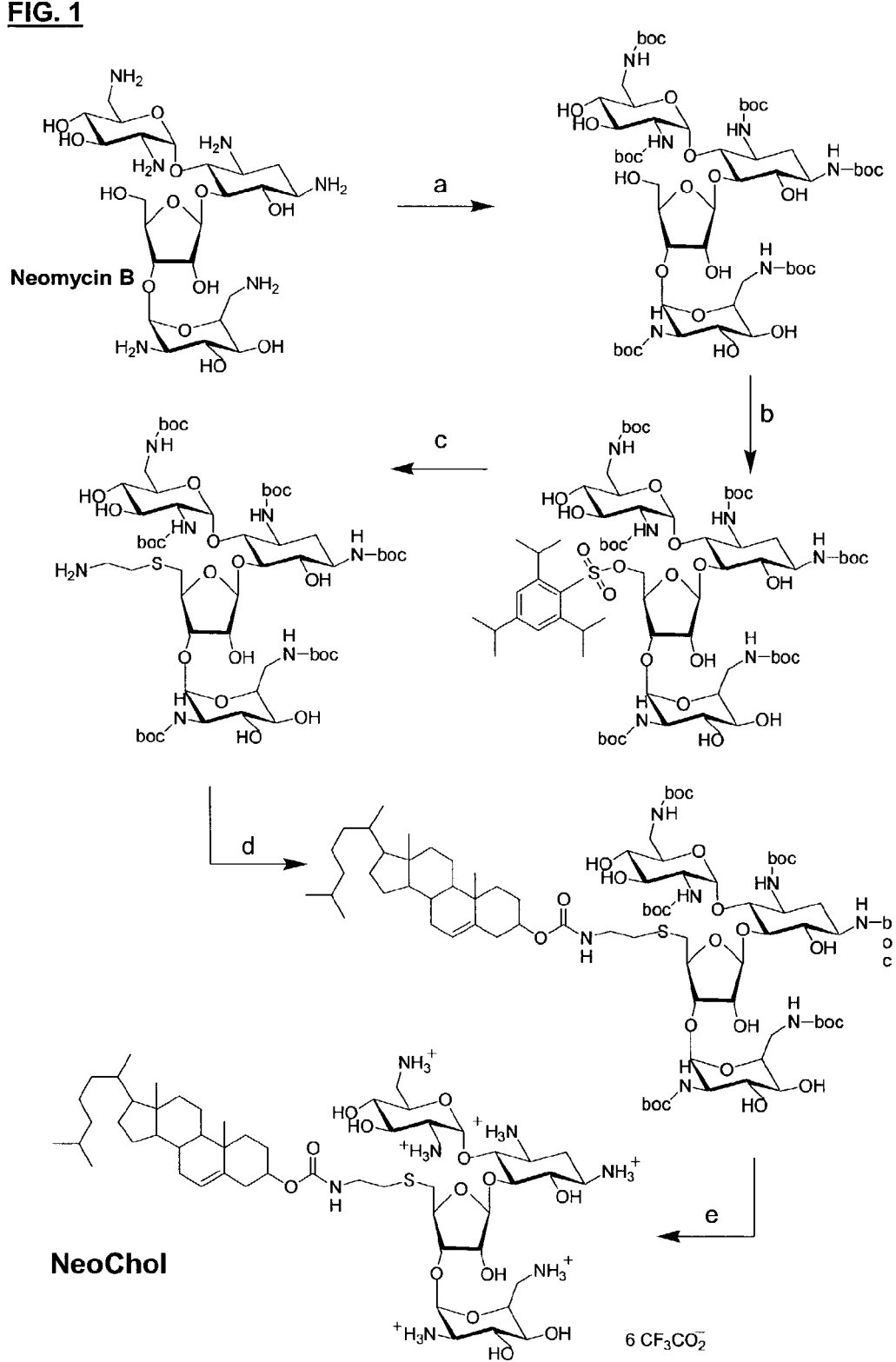

Cytotoxicity of the KanaChol/DNA formulations at various charge ratios

Cytotoxicity of the KanaChol/DOPE/DNA formulations at various charge ratios

FIG. 6

Expression of luciferase (RLU/mg proteins) in various mammalian cell lines transfected with KanaChol or KanaChol/DOPE (molar ratio 1:1)

| Cell line | Species/ Tissue type | KanaChol | KanaChol/ DOPE |
|---|---|---|---|
| NIH 3T3 | Mouse fibroblasts | $4.5 \times 10^5$ | $4.3 \times 10^6$ ($\pm 3 \times 10^6$) |
| A549 | Human lung carcinoma | $2 \times 10^5$ ($\pm 0.3 \times 10^5$) | $8.5 \times 10^6$ ($\pm 6 \times 10^6$) |
| 16HBE | Human bronchial epithelium | $3.4 \times 10^3$ ($\pm 1.7 \times 10^3$) | $3 \times 10^6$ ($\pm 0.4 \times 10^6$) |
| HepG2 | Human hepatoblastoma | $5 \times 10^4$ ($\pm 4 \times 10^4$) | $5.2 \times 10^6$ ($\pm 3.2 \times 10^6$) |
| MITC | Human thymic myoid cells | $3.2 \times 10^6$ ($\pm 0.3 \times 10^6$) | $1.5 \times 10^7$ ($\pm 0.5 \times 10^7$) |

FIG. 7

Expression of luciferase in mammalian cell lines transfected with TGKC/DOPE liposomes

| Cell line | Luciferase Activity (RLU / mg proteins) |
|---|---|
| COS | $4.5 \times 10^6$ ($\pm 1 \times 10^6$) |
| HeLa | $5 \times 10^5$ ($\pm 2.5 \times 10^5$) |
| NIH 3T3 | $5.2 \times 10^5$ ($\pm 2 \times 10^5$) |
| MITC | $5.6 \times 10^6$ ($\pm 1 \times 10^6$) |

FIG. 8

IN VITRO TRANSFECTING ACTIVITY OF NEOCHOL/DNA FORMULATIONS

| Cell line | Transfection efficiency of Neochol/DNA |
|---|---|
| HEK293 | efficient, but less efficient than with Neochol/DOPE/DNA |
| NIH 3T3 | efficient, but less efficient than with Neochol/DOPE/DNA |
| HeLa | efficient, but less efficient than with Neochol/DOPE/DNA |
| COS | efficient, but less efficient than with Neochol/DOPE/DNA |
| 16HBE | efficient, but less efficient than with Neochol/DOPE/DNA, except at the high charge ratio |

FIG. 10

CAT expression in airways of mice following intranasal instillation of KanaChol/DOPE/DNA lipoplexes stabilized with Chol-PEG

| Type of vector | CAT expression in the trachea (ng/100 mg proteins) | CAT expression in the lungs (ng/100 mg proteins) |
|---|---|---|
| KanaChol/DOPE | 0.8 ± 0.9 | 6.1 ± 3.5 |
| Nonformulated DNA | 0.03 ± 0.05 | 0.14 ± 0.16 |

LIPID DERIVATIVES OF AMINOGLYCOSIDES

The present application claims priority under 35 U.S.C. §119(e) of U.S. Provisional Application No. 60/331,452, filed Nov. 16, 2001, the disclosure of which is expressly incorporated by reference herein. The present application also claims priority under 35 U.S.C. §119 of French Application No. 01/11199, filed Aug. 29, 2001, the disclosure of which is expressly incorporated by reference herein.

The present invention relates to novel compounds which allow the transfer of nucleic acids into cells. More precisely, these novel compounds are lipid derivatives of aminoglycosides and their polyguanidylated derivatives. They are useful for the in vitro, ex vivo, or in vivo transfection of nucleic acids into various cell types.

With the development of biotechnology it has become necessary to efficiently transfer nucleic acids into cells. This may involve transferring nucleic acids into cells in vitro, for example for producing recombinant proteins, or in the laboratory, for studying the regulation of gene expression, cloning genes or any other manipulation involving DNA. It may also involve transferring nucleic acids into cells in vivo, for example for the creation of transgenic animals, the production of vaccines, labeling studies or also therapeutic approaches. It may also involve transferring nucleic acids into cells ex vivo, in approaches for bone marrow transplantation or for immunotherapy, or other methods involving the transfer of genes into cells removed from an organism, with a view to subsequently readministering them.

Today, several methods are proposed for the intracellular delivery of exogenous genetic material. One of them, in particular, is based on the use of nonviral vectors, which constitutes a very advantageous alternative compared to viral methods, which are not entirely free of risks. These synthetic vectors have two main functions: to complex and compact the nucleic acid to be transfected, and to promote its passage across the plasma membrane and, optionally, across the nuclear envelope.

Several families of synthetic vectors have thus been developed, such as for example polymers or biochemical vectors (consisting of a cationic protein associated with a cellular receptor), but considerable progress has especially been accomplished with the development of lipofectants, and more particularly cationic lipids. It has thus been demonstrated that cationic lipids, due to their overall positive charge, interfere spontaneously with DNA, which is negative overall, forming nucleolipid complexes capable of both protecting the DNA against nucleases and attaching to cell membranes for intracellular release of the DNA. Thus, most of the nonviral vectors developed to date are based on amine protonation to allow binding to the DNA.

Various types of cationic lipids have been synthesized to date: lipids comprising a quaternary ammonium group (for example DOTMA, DOTAP, DMRIE, DLRIE, etc.), lipopolyamines, such as for example DOGS, DC-chol, or the lipopolyamines disclosed in patent application WO 97/18185, lipids which combine both a quaternary ammonium group and a polyamine, such as DOSPA, or lipids comprising various other cationic entities derived from amines, in particular amidinium groups (for example ADPDE, ADODE or the lipids of patent EP 0 888 379 B1 or U.S. Pat. No. 6,143,729, in particular BGTC).

Although the structure/activity relationships of cationic lipids are not yet really understood, it is generally considered that the nature of the cationic component has a major impact on the transfection activity, although it is the nature and the physicochemical properties of the whole molecule (such as the hydrophobicity/hydrophilicity balance, the interactions with colipids, etc.) which determine the efficiency of a given cationic lipid in fine (see, for example, Felgner et al., *Am. Chem. Soc.*, 1996, pp. 177-190).

For this reason, in the past few years, a great deal of effort has been spent in developing cationic lipids which have novel cationic entities. The object of the present invention is precisely to provide novel transfecting compounds which are original by virtue of their cationic component consisting of aminoglycosides or of their polyguanidylated derivatives, and which can be used effectively for the in vitro, ex vivo or in vivo transfection of nucleic acids. These novel compounds are particularly advantageous because the aminoglycosides can interact with three-dimensional substructures found in a large variety of RNA molecules (Walter et al., *Curr. Opin. Chem. Biol.*, 1999, 3, pp. 694-704) and they therefore constitute novel cationic groups which have structural characteristics particularly suitable for synthesizing a large variety of transfecting compounds. Specifically, aminoglycosides are multifunctional compounds containing up to 6 amino groups and several hydroxyl functions. Selective acylation of one or more of these groups has therefore made it possible to obtain aminoglycosides which have the lipophilic properties required for use in transfection. In addition, aminoglycosides can be easily polyguanidylated in a single step, which makes it possible, for example, to synthesize transfecting compounds having guanidinium groups in place of amines, in their cationic component. Finally, these novel transfecting compounds are also particularly advantageous from a pharmaceutical point of view since the aminoglycosides which constitute their cationic component are natural compounds which are already widely used in pharmacy as antibiotics, their antibacterial activity in fact being derived from their interaction with prokaryotic rRNAs (Moazed et al., *Nature*, 1987, 327, pp. 389-394; Puhrohit et al., *Nature*, 1994, 370, pp. 659-662).

A first subject of the present invention is thus transfecting compounds, characterized in that they comprise an aminoglycoside linked to a lipid via a spacer, and their polyguanidylated derivatives.

In particular, the subject of the present invention is transfecting compounds of the general formula (I):

$$A\text{-}Y\text{-}L \qquad (I)$$

in which:
  A represents an aminoglycoside or its polyguanidylated derivative,
  Y represents a spacer, and
  L represents:
    either a radical —(R$_1$)R$_2$ wherein R$_1$ and R$_2$ represent, independently of one another, a hydrogen atom or a fatty aliphatic chain or R$_1$ or R$_2$ is absent, it being understood that at least one of R$_1$ and R$_2$ represents a fatty aliphatic chain,
    or a radical —N—R$_3$ or —O—R$_3$, wherein R$_3$ represents a steroidal derivative.

For the purpose of the present invention, the term "aminoglycoside" (or "aminoside") is intended to mean a natural heteroside formed by the combining of a genin of the aminocyclitol group with generally several saccharides, at least one of which is an aminosugar (osamine). They may therefore be considered to be pseudooligosaccharides having antibiotic properties. By way of example of suitable aminoglycosides, mention may be made of amikacin, arbekacin, deoxyhydrostreptomycin, destomycin A, dibekacin, dihydrostreptomycin, genticin, gentamycin, hygromycin, isepamycin, kanamycin, micronomycin, paromomycin, ribostamycin, streptomycin, streptonicozide, neomycin, tobramycin, sisomycin or semisynthetic aminosides.

The polyguanidylated derivative of an aminoglycoside according to the invention is the aminoglycoside for which the amino functions have been replaced with guanidinium functions. For example, the polyguanidylated derivative of kanamycin, or guanidinokanamycin, has been described by Baker et al. (*J. Org. Chem.*, 2000, 65, pp. 9054-9058).

According to the present invention, the term "spacer" is intended to mean any chemical group which makes it possible both to form the bond between the aminoglycoside or its polyguanidylated derivative and the lipid component of the molecule, and to distance these two components in order to reduce any undesired interaction between them. Consequently, the spacer is a difunctional chemical group which may, for example, consist of one or more chemical functions chosen from alkyls having 1 to 6 carbon atoms, ketone, ester, ether, amino, amide, amidine, carbamate or thiocarbamate functions, glycerol, urea, thiourea or aromatic rings. For example, the spacer may be chosen from the radicals of formula:

—C(O)—

—NH—C(O)—CH$_2$—CH$_2$—

—W—(CH$_2$—)$_k$—W'- or: —(CH$_2$—)$_i$—W—(CH$_2$)$_j$— in which i, j and k are integers chosen between 1 and 6 inclusive, and W and W' are groups, which may be identical or different, chosen from ketone, ester, ether, amino, amide, amidine, carbamate or thiocarbamate functions, glycerol, urea, thiourea or aromatic rings.

For the purpose of the present invention, the term "fatty aliphatic chains" is intended to mean saturated or unsaturated alkyl radicals containing 10 to 22 carbon atoms and optionally containing one or more hetero atoms, provided that said fatty aliphatic chains have lipid properties. They may be linear or branched alkyl radicals containing 10 to 22 carbon atoms and 1, 2 or 3 unsaturations. The alkyl radicals may comprise 10, 12, 14, 16, 18, 20 or 22 carbon atoms. Mention may be made of the aliphatic radicals —(CH$_2$)$_{11}$CH$_3$, —(CH$_2$)$_{13}$CH$_3$, —(CH$_2$)$_{15}$CH$_3$ and —(CH$_2$)$_{17}$CH$_3$.

For the purpose of the present invention, the term "steroidal derivatives" is intended to mean polycyclic compounds of the cholestane type. These compounds may or may not be natural and may be chosen from cholesterol, cholestanol, 3-α-5-cyclo-5-α-cholestan-6-β-ol, cholic acid, cholesteryl formiate, cholestanyl formiate, 3-α-5-cyclo-5-α-cholestan-6-β-yl formiate, cholesterylamine, 6-(1,5-dimethylhexyl)-3a,5a-dimethylhexadecahydrocyclopenta[a]cyclopropa[2,3]cyclopenta[1,2-f]naphthalen-10-ylamine or cholestanylamine.

The transfecting compounds, for which A and Y are as defined above in general formula (I) and L is a radical —OR$_3$ wherein R$_3$ represents a steroidal derivative, constitute a subclass of transfecting compounds which may be used for the purpose of the present invention.

The transfecting compounds according to the present invention may be chosen from the compounds of general formula (I) for which A and Y are as defined above and L is a radical —OR$_3$, wherein R$_3$ represents a cholesterol radical.

Transfecting compounds include 3β[6'-kanamycin-carbamoyl]cholesterol ("KanaChol") of formula:

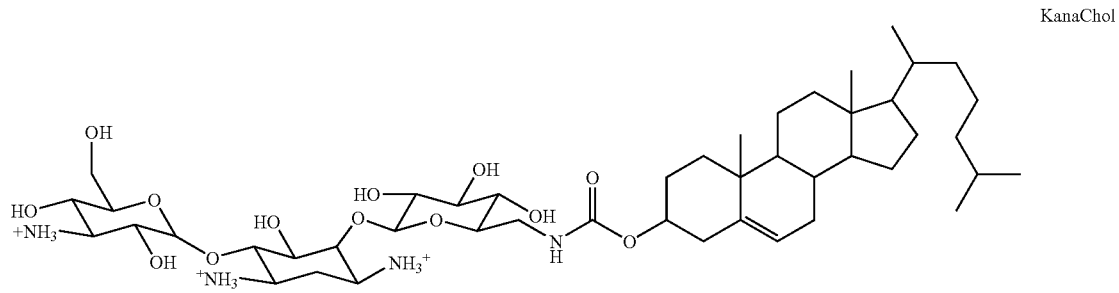

KanaChol and 3β[6'-(1,3,3"-triguanidino)kanamycin-carbamoyl]cholesterol ("TGKC") of formula:

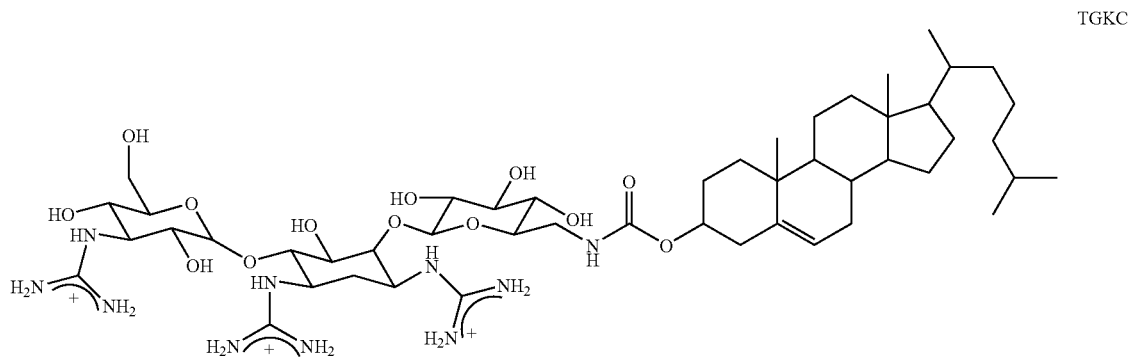

TGKC and the (5"-aminoethylsulfanyl) neomycin carbamoyl cholesterol of formula:

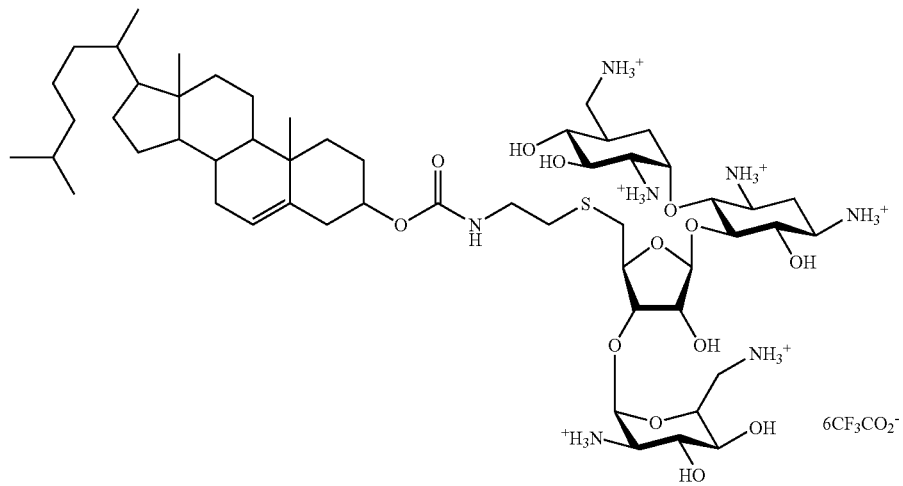

NeoChol

It is understood that the present invention also relates to the isomers of the products of general formula (I) when they exist, and also the mixtures thereof, or the salts thereof.

The compounds of the invention may be in the form of nontoxic and pharmaceutically acceptable salts. These nontoxic salts comprise salts with inorganic acids (for example hydrochloric, sulfuric, hydrobromic, phosphoric, nitric acid) or with organic acids (acetic, propionic, succinic, maleic, hydroxymaleic, benzoic, fumaric, methanesulfonic, trifluoroacetic or oxalic acid).

The compounds of general formula (I) according to the present invention are prepared by carrying out the following steps, in the order presented or according to any other known and equally suitable variant, using techniques of conventional organic synthesis, in solution or on solid supports, which are well known to those skilled in the art:

1) Production of the Lipid Component L

When the lipid component L of the compounds of general formula (I) is represented by a radical —(R$_1$)R$_2$ attached, for example, to a nitrogen atom of the spacer, the amine of formula HN(R$_1$)R$_2$ is first of all formed. Said amine may be obtained by condensation of a carboxylic acid and an amine, one containing the substituent R$_1$ and the other the substituent R$_2$, so as to form the corresponding amide, followed by reduction of said amide.

The formation of the amide may be carried out by mixing the constituents and melting by heating to a temperature greater than the melting temperature of the substances involved, in general between 20° C. and 200° C., and then eliminating the water produced by dehydration of the medium; or alternatively in the presence of a desiccating agent, such as, for example, phosphorus pentoxide or any other substance which can absorb water. This intermediate amide may also be formed using a variant of this method or any other method of amide formation (such as, for example, coupling of the peptide type) involving carboxylic acids or their derivatives, conditions and reagents which are varied [R. C. Larock, Comprehensive Organic Transformations, VCH editors] and well known to those skilled in the art.

Reduction of the amide obtained above to an amine of formula HN(R$_1$)R$_2$ may be carried out, for example, using a reducing agent such as lithium aluminum hydride, or any other hydride or reducing agent which is effective in this case. The procedure may then be carried out in a nonprotic solvent (for example tetrahydrofuran or ethers), at a temperature lower than the boiling temperature of the solvent and under a dry and/or inert atmosphere.

According to another variant, the lipid component denoted as NH(R$_1$)R$_2$ may be commercially available.

When the lipid component L of the compounds of general formula (I) is represented by a radical —NR$_3$ or —OR$_3$, it may be chosen from commercially available products.

2) Grafting of the Spacer Y

The spacer Y is then attached to the lipid component L obtained in the preceding step, according to conventional techniques known to those skilled in the art. According to one variant, an amide bond is formed by N-acylation of the lipid component L in a suitable solvent, such as dichloromethane, chloroform, tetrahydrofuran or any other ether, at a temperature lower than the boiling temperature of the solvent, and under a dry and/or inert atmosphere. This reaction may take place in the presence of an amine base, such as N,N-dimethylaminopyridine, or in the presence of this base mixed with nonnucleophilic amine bases, such as triethylamine or ethyldiisopropylamine. Pyridine may also be used, alone or mixed with another base, diluted with one of the solvents mentioned or used, itself, as a solvent.

According to another variant, when the lipid component L represents a radical —OR$_3$, treatment, with phosgene, of the corresponding alcohol R$_3$OH gives a chloroformiate (sometimes commercially available).

3) Grafting of the Aminoglycoside

The grafting of the aminoglycoside onto the Y-L combination is carried out using the amine and/or hydroxyl functions carried by the aminoglycoside, whether they are present in the natural compound or originate from a modification produced according to the conventional methods known to those skilled in the art.

According to a variant, an amide bond is formed by N-acylation of an amine function of the aminoglycoside with the Y-L combination suitably activated according to the conventional methods used to create a peptide bond.

When the lipid component L of the compounds of general formula (I) is represented by the radical —OR$_3$, a possibility consists in linking the components A and L via a carbamate bond obtained by treating the aminoglycoside with the chloroformiate, sometimes commercially available, of the alcohol $R_3OH$. This reaction takes place in a suitable solvent, such as dichloromethane, chloroform, tetrahydrofuran, dimethylformamide or any other ether, at a temperature lower than the boiling temperature of the solvent, under a dry and/or inert atmosphere and in the presence of a nonnucleophilic amine base, such as triethylamine, ethyldiisopropylamine or pyridine.

In general, the aminoglycosides used in the context of the invention are commercially available.

4) Transformation of the Amines into Quanidines

The transformation of the amine functions of the aminoglycoside into guanidine functions may be easily carried out according to the techniques known to those skilled in the art, such as by using the techniques described by Baker et al. (*J. Org. Chem.*, 2000, 65, pp. 9054-8), Luedtke et al. (*J. Am. Chem.*, 2000, 122, pp. 12035-12036) or Iwanowicz et al. (*Synth. Commun.* 1993, 23, pp. 1443-1445). Advantageously, the technique and the reagents described by Iwanowicz et al. (*Synth. Commun.* 1993, 23, pp. 1443-1445) are used.

Naturally, when the various substituents may interfere with the reaction, they may be protected beforehand with radicals which are compatible and which can be introduced and eliminated without affecting the rest of the molecule. This may be carried out according to the conventional methods known to those skilled in the art, such as according to the methods described in T. W. Greene, *Protective Groups in Organic Synthesis*, Wiley-Interscience, in McOmie, *Protective Groups in Organic Chemistry*, Plenum Press, or in P. J. Kocienski, *Protecting Groups*, Thieme.

Moreover, each step of the preparation process may be followed, where appropriate, by steps for separating and purifying the compound obtained, according to any method known to those skilled in the art.

Another subject of the invention relates to compositions comprising a transfecting compound according to the invention and a nucleic acid. The respective amounts of each component may be easily adjusted by those skilled in the art depending on the transfecting compound used, on the nucleic acid and on the desired applications (in particular on the type of cell to be transfected).

For the purpose of the invention, the term "nucleic acid" is intended to mean both a deoxyribonucleic acid and a ribonucleic acid. They may be natural or artificial sequences, and in particular genomic DNA (gDNA), complementary DNA (cDNA), messenger RNA (mRNA), transfer RNA (tRNA) or ribosomal RNA (rRNA), hybrid sequences such as DNA/RNA chimeroplasts, or synthetic or semi-synthetic sequences, modified oligonucleotides or unmodified oligonucleotides. These nucleic acids may be of human, animal, plant, bacterial, viral, etc. origin. They may be obtained using any technique known to those skilled in the art, such as by screening libraries, by chemical synthesis or by mixed methods including the chemical or enzymatic modification of sequences obtained by screening libraries. They may be modified chemically. In general, they contain at least about 10, 20, 50 or 100 consecutive nucleotides, and generally at least about 200 consecutive nucleotides. More generally, they contain at least about 500 consecutive nucleotides.

With regard more particularly to the deoxyribonucleic acids, they may be single-stranded or double-stranded, as well as short oligonucleotides or longer sequences. In particular, the nucleic acids advantageously comprise plasmids, vectors, episomes, expression cassettes, etc. These deoxyribonucleic acids may carry a prokaryotic or eukaryotic origin of replication which may or may not be functional in the target cell, one or more marker genes, sequences which regulate transcription or replication, genes of therapeutic interest, antisense sequences which may or may not be modified, regions for binding to other cellular components, etc.

The nucleic acid may comprise one or more genes of therapeutic interest under the control of regulatory sequences, for example one or more promoters and a transcriptional terminator which are active in the target cells.

For the purpose of the invention, the expression "gene of therapeutic interest" is intended to mean any gene encoding a protein product which has a therapeutic effect. The protein product thus encoded may be a protein or a peptide. This protein product may be exogenous, homologous, or endogenous with respect to the target cell, i.e., a product which is normally expressed in the target cell when the latter does not show any pathological condition. In this case, the expression of a protein makes it possible, for example, to compensate for insufficient expression in the cell or the expression of a protein which is inactive or weakly active due to a modification, or to overexpress the said protein. The gene of therapeutic interest may also encode a mutant of a cellular protein, which has increased stability, modified activity, etc. The protein product may also be heterologous with respect to the target cell. In this case, an expressed protein may, for example, add to or introduce deficient activity in the cell, making it possible for it to combat a pathological condition, or stimulate an immune response.

Among the therapeutic products for the purpose of the present invention, mention may be made of enzymes, blood derivatives, hormones, lymphokines and cytokines and inhibitors thereof or antagonists thereof (interleukins, interferons, TNF, interleukin 1 antagonists, soluble receptors for interleukin 1 and TNFα, etc.: FR 92/03120), growth factors, neurotransmitters or their precursors or synthetic enzymes, trophic factors (BDNF, CNTF, NGF, IGF, GMF, aFGF, bFGF, VEGF-A, VEGF-B, NT3, NT5, HARP/pleitrophin, etc.) apolipoproteins (ApoAI, ApoAIV, ApoE, etc.: FR 93/05125), dystrophin or a minidystrophin (FR 91/11947), the CFTR protein associated with cystic fibrosis, tumor suppressor genes (p53, Rb, Rap1A, DCC, k-rev, etc.: FR 93/04745), genes encoding factors involved in clotting (factors VII, VIII and IX), genes involved in DNA repair, suicide genes (thymidine kinase, cytosine deaminase), genes for hemoglobin or for other protein transporters, metabolic enzymes, catabolic enzymes, etc.

The nucleic acid of therapeutic interest may also be an antisense sequence or gene or a DNA encoding an RNA with a ribozyme function, the expression of which in the target cell makes it possible to control the expression of genes or the transcription of cellular mRNAs. Such sequences may, for example, be transcribed, in the target cell, into RNAs complementary to cellular mRNAs and thus block their translation into protein, according to the technique described in patent EP 140 308. The therapeutic genes also comprise the sequences encoding ribozymes, which are capable of selectively destroying target RNAs (EP 321 201).

As indicated above, the nucleic acid may also comprise one or more genes encoding an antigenic peptide capable of generating, in humans or animals, an immune response. In this particular embodiment, the invention allows the production of vaccines or the carrying out of immunotherapeutic treatments, applied to humans or to animals, in particular for treating or preventing infections, for example viral or bacterial infections, or cancers. They may be antigenic peptides specific for the Epstein-Barr virus, for the HIV virus, for the hepatitis B virus (EP 185 573), for the pseudorabies virus, for the syncitia forming virus or for other viruses, or antigenic peptides specific for tumors (EP 259 212).

The nucleic acid may also comprise sequences which allow the expression of the gene of therapeutic interest and/or of the gene encoding the antigenic peptide, in the desired cell or organ. They may be sequences which are naturally responsible for the expression of the gene in question when these sequences are capable of functioning in the infected cell. They may also be sequences of different origin (responsible for the expression of other proteins or even synthetic). They may be promoter sequences of eukaryotic or viral genes. For example, they may be promoter sequences derived from the genome of the cell intended to be infected. Similarly, they may be promoter sequences derived from the genome of a virus. In this regard, mention may be made, for example, of the E1A, MLP, CMV, RSV, etc. gene promoters. In addition, these expression sequences may be modified by adding activation sequences, regulatory sequences, etc. It may also be an inducible or repressible promoter.

Moreover, the nucleic acid may also comprise, in particular upstream of the gene of therapeutic interest, a signal sequence which directs the therapeutic product synthesized into the secretory pathways of the target cell. This signal sequence may be the natural signal sequence of the therapeutic product, but it may also be any other functional signal sequence or an artificial signal sequence. The nucleic acid may also comprise a signal sequence which directs the therapeutic product synthesized toward a particular compartment of the cell.

The compositions according to the invention may also comprise one or more adjuvants capable of associating with the transfecting compound/nucleic acid complexes and improving the transfecting power thereof. In another embodiment, the present invention therefore relates to compositions comprising a nucleic acid, a transfecting compound as described above and at least one adjuvant capable of associating with the transfecting compound/nucleic acid complexes and improving the transfecting power thereof. These adjuvants which make it possible to increase the transfecting power of the compounds according to the present invention may be chosen from lipids (for example neutral lipids, such as phospholipids), peptides (for example histone, nucleolin or protamine derivatives such as those described in WO 96/25508), proteins (for example proteins of the HMG type such as those described in WO 97/12051) and/or polymers (for example polymers which make it possible to turn the transfecting compound/nucleic acid formulations into "stealth" formulations, such as polyethylene glycol (PEG) introduced into the formulation on its own or in a form attached to a lipid in order to colloidally stabilize the transfecting compound/nucleic acid formulations, for example PEG-cholesterol). From this point of view, the compositions of the invention may comprise, as an adjuvant, one or more neutral lipids which may have the property of forming lipid aggregates. The term "lipid aggregate" is a generic term which includes liposomes of all types (both unilamellar and multilamellar) and also micelles or more amorphous aggregates.

The neutral lipids used in the context of the present invention may be lipids containing two fatty chains. Use may be made of natural or synthetic lipids which are zwitterionic or lacking ionic charge under physiological conditions. They may be chosen from dioleoylphosphatidyl ethanolamine (DOPE), oleoylpalmitoylphosphatidylethanolamine (POPE), distearoyl-, dipalmitoyl- and dimirystoylphosphatidylethanolamines and also the derivatives thereof which are N-methylated 1 to 3 times, phosphatidylglycerols, diacylglycerols, glycosyldiacylglycerols, cerebrosides (such as galactocerebrosides), sphingolipids (such as sphingomyelins) or asialogangliosides (such as asialoGM1 and asialoGM2). According to an alternative, the lipid adjuvants used in the context of the present invention are chosen from DOPE, dioleoylphosphatidylcholine (DOPC), cholesterol or the lipid derivatives of nonionic surfactants, such as PEG-cholesterol.

These various lipids may be obtained either by synthesis or by extraction from organs (for example the brain) or from eggs, using conventional techniques well known to those skilled in the art. For example, the extraction of natural lipids may be carried out using organic solvents (see also Lehninger, Biochemistry).

The compositions of the invention may comprise from about 0.01 to 20 equivalents of adjuvant per equivalent of nucleic acid in mol/mol, and generally from about 0.5 to 5 molar equivalents.

According to another alternative, the adjuvants cited above make it possible to improve the transfecting power of the compositions according to the present invention. The peptides, the proteins or certain polymers, such as polyethylene glycol, may be conjugated to the transfecting compounds according to the invention, and not simply mixed. The PEG may be attached covalently to the lipid derivatives of aminoglycoside according to the present invention either at a remaining amine of the aminoglycoside or at the hydroxyl radicals of the aminoglycoside.

According to one embodiment, the compositions according to the present invention also comprise a targeting element which makes it possible to direct the transfer of the nucleic acid. This targeting element may be an extracellular targeting element which makes it possible to direct the transfer of the nucleic acid toward certain desired cell types or tissues (tumor cells, hepatic cells, hematopoietic cells, etc.). It may also be an intracellular targeting element which makes it possible to direct the transfer of the nucleic acid toward certain preferred cellular compartments (mitochondria, nucleus, etc.). The targeting element may be mixed with the transfecting compounds according to the invention and with the nucleic acids and, in this case, the targeting element is preferably attached covalently to a fatty aliphatic chain (at least 10 carbon atoms) or to a polyethylene glycol. According to another alternative, the targeting element is covalently attached to the transfecting compound according to the invention, either on one of the chemical functions which make up the spacer Y, or at the end of the lipid component (for example at the end of $R_1$ and/or $R_2$ when they represent fatty aliphatic chains), or directly on the aminoglycoside at one of the remaining amines or at the hydroxyl radicals. Finally, the targeting element may also be attached to the nucleic acid, as specified previously.

Among the targeting elements which can be used in the context of the invention, mention may be made of sugars, peptides, proteins, oligonucleotides, lipids, neuromediators, hormones, vitamins or derivatives thereof. Generally, they are sugars, peptides, vitamins or proteins such as, for example, antibodies or antibody fragments, cell receptor ligands or fragments thereof, receptors or receptor fragments. For example, they may be ligands for growth factor receptors, for cytokine receptors, for receptors of the cellular lectin type or for folate receptors, or ligands containing an RGD sequence with an affinity for adhesion protein receptors such as integrins. Mention may also be made of transferrin receptors, HDL receptors and LDL receptors or the folate transporter. The targeting element may also be a sugar which makes it possible to target lectins such as the receptors for asialoglycoproteins or for sialidized species, such as sialyl Lewis X, or an Fab antibody fragment or a single-chain antibody (ScFv).

A subject of the invention is also the use of the transfecting compounds according to the present invention, for transferring nucleic acids into cells in vitro, in vivo, or ex vivo. More precisely, a subject of the present invention is the use of the transfecting compounds as defined in the context of the invention, for preparing a medicinal product intended to treat diseases, such as diseases which result from a deficiency in a protein or nucleic acid product. The polynucleotide contained in said medicinal product encodes said protein or nucleic acid product, or constitutes said nucleic acid product, capable of correcting said diseases in vivo or ex vivo.

For uses in vivo, for example in therapy or for studying gene regulation or creating animal models of pathological conditions, the compositions according to the invention may be formulated with a view to topical, cutaneous, oral, rectal, vaginal, parenteral, intranasal, intravenous, intramuscular, subcutaneous, intraocular, transdermal, intratracheal, intraperitoneal, etc. administration. The compositions of the invention may contain a vehicle which is pharmaceutically acceptable for an injectable formulation, such as for direct injection into the desired organ, or for topical administration (on skin and/or mucous membrane). They may be sterile, isotonic solutions or dry compositions, such as lyophilized compositions, which, by adding, as appropriate, sterilized water or physiological saline, allow injectable solutes to be made up. The doses of nucleic acids used for the injection and also the number of administrations may be adjusted depending on various parameters, and depending on the method of administration used, on the pathological condition in question, on the gene to be expressed, or on the desired duration of the treatment.

With regard to the method of administration, it may be either a direct injection into the tissues, for example into the tumors, or an injection into the circulatory system, or it may involve treating cells in culture followed by their reimplantation in vivo, by injection or transplantation. The relevant tissues in the context of the present invention are, for example, muscles, skin, brain, lungs, trachea, liver, spleen, bone marrow, thymus, heart, lymph, blood, bones, cartilage, pancreas, kidneys, bladder, stomach, intestines, testicles, ovaries, rectum, nervous system, eyes, glands, connective tissues, etc.

Another subject of the present invention relates to a method for transferring nucleic acids into cells, comprising the following steps:

(1) bringing the nucleic acid into contact with a transfecting compound according to the present invention, so as to form a complex, and (2) bringing the cells into contact with the complex formed in (1).

The invention also relates to a method for treating the human or animal body, comprising the following steps:

(1) bringing the nucleic acid into contact with a transfecting compound according to the present invention, so as to form a complex, and (2) bringing the cells of the human or animal body into contact with the complex formed in (1).

The cells can be brought into contact with the complex by incubating the cells with said complex (for in vitro or ex vivo uses) or by injecting the complex into an organism (for in vivo uses). In general, the amount of nucleic acid intended to be administered depends on very many factors, such as for example the disease to be treated or prevented, the very nature of the nucleic acid, the strength of the promoter, the biological activity of the product expressed by the nucleic acid, the physical condition of the individual or of the animal (weight, age, etc.), the method of administration and the type of formulation. In general, the incubation is carried out in the presence of, for example, from about 0.01 to 1000 µg of nucleic acid per $10^6$ cells. For administration in vivo, nucleic acid doses ranging from about 0.01 to 50 mg may, for example, be used. The administration may be carried out as a single dose or a repeated dose with periods in between.

When the compositions of the invention also contain one or more adjuvants as defined above, the adjuvant(s) is (are) mixed beforehand with the transfecting compound according to the invention and/or with the nucleic acid. Alternatively, the adjuvant(s) may be administered prior to administration of the nucleolipid complexes.

According to another advantageous alternative, the tissues may be subjected to chemical or physical treatment intended to improve the transfection. In the case of physical treatment, this may use electrical impulses as in the case of electrotransfer, or mechanical forces as in the case of "sodoporation".

The present invention thus provides an advantageous method for transferring nucleic acids in vivo, such as for the treatment of diseases, comprising the in vivo or in vitro administration of a nucleic acid encoding a protein, or possibly being transcribed into a nucleic acid, which is capable of correcting said disease, said nucleic acid being associated with a transfecting compound according to the invention under the conditions defined above.

The transfecting compounds of the invention are useful for transferring nucleic acids into primary cells or into established lines. They may be fibroblast cells, muscle cells, nerve cells (neurons, astrocytes, glial cells), hepatic cells, hematopoietic cells (lymphocytes, CD34 cells, dendritic cells, etc.), epithelial cells, etc., in differentiated form or pluripotent form (precursors).

Another subject of the present invention also relates to the transfection kits which comprise one or more transfecting compounds according to the invention and mixtures thereof. Such kits may be in the form of packaging containing compartments which can take various containers, such as for example vials or tubes. Each of these containers comprises the various elements required to carry out the transfection, individually or mixed: for example, one or more transfecting compound(s) according to the invention, one or more nucleic acid(s), one or more adjuvant(s), cells, etc.

Besides the arrangements above, the present invention also comprises other characteristics and/or advantages which will emerge from the following examples and figures, which should be considered as illustrating the invention without limiting the scope thereof. In particular, the Applicants provide, with no limitation being implied, an operating protocol and also reaction intermediates which can be used for preparing the transfecting compounds according to the invention. Of course, it is within the scope of those skilled in the art to use this protocol or intermediate products as a basis for developing similar processes with a view to producing these same compounds.

FIGURES

FIG. 1: Schematic representation of the reactions of synthesis of (5″-aminoethyl sulfanyl)neomycin carbamoyl cholesterol trifluoroacetate (e.g., example 3). a) $Boc_2O$, $Et_3N$, $DMF/H_2O$, 60° C., 88%. b) 2,4,6-Triisopropylbenzenesulfonyle chlorure, Pyridine, 50%. c) $HS-CH_2-CH_2-NH_2$, NaOEt/EtOH, 46%. d) cholesteryl chloroformiate, $Et_3N$, THF/DMF, 52%. e) trifluoroacetic acid, T<0° C., 40 nm, 98%.

Figure 2:
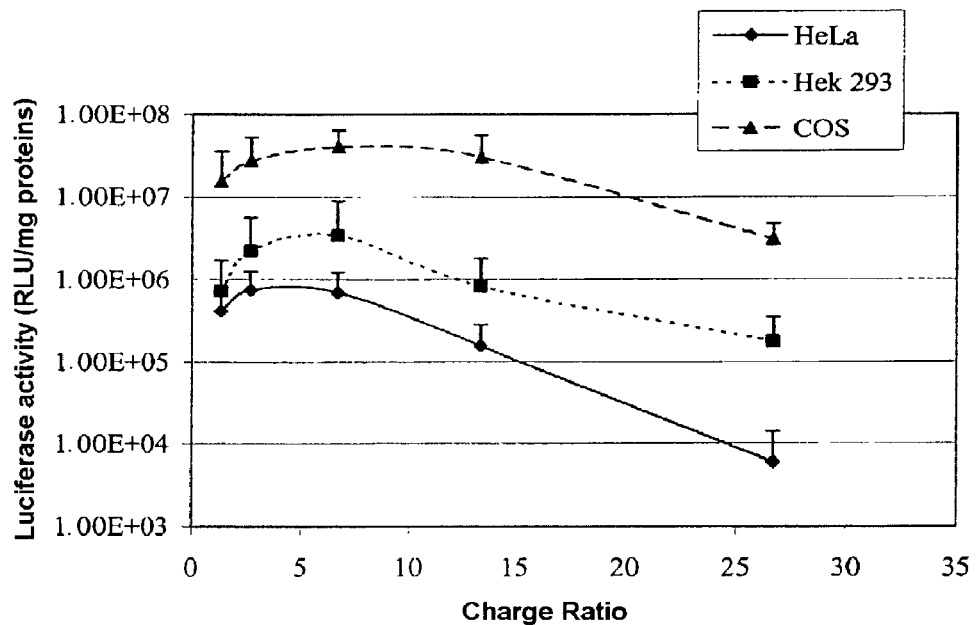

FIG. 2: Dose-response curves of the in vitro transfection activity of the transfecting compound "KanaChol". The expression of the reporter gene is indicated as a function of the charge ratio of the lipoplexes formed with the plasmid DNA. The HeLa, HEK293 and COS cells were transfected in accordance with the protocol described in Example 3 using lipoplexes prepared by mixing 5 µg of plasmid DNA expressing luciferase with the required amount of lipid. The data are expressed in relative light units (RLU) per mg of cellular proteins.

Figure 3:
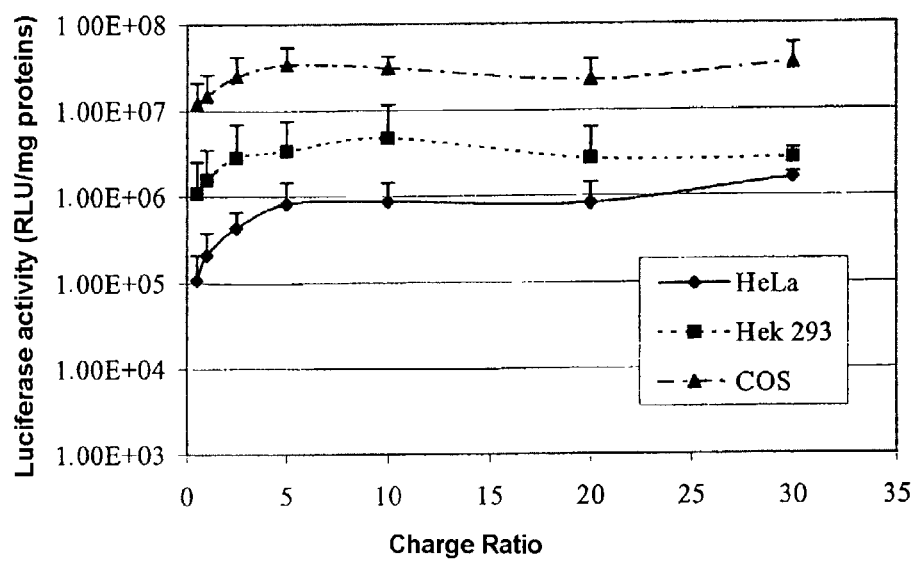

FIG. 3: Dose-response curves of the in vitro transfection activity of the KanaChol/DOPE (molar ratio 1:1) liposomes. The expression of the reporter gene is indicated as a function of the charge ratio of the lipoplexes formed with the plasmid DNA. The HeLa, HEK293 and COS cells were transfected in accordance with the protocol described in Example 4 using lipoplexes prepared by mixing 5 µg of plasmid DNA expressing luciferase with the required amount of lipid to form lipoplexes characterized by the charge ratio indicated. The data are expressed in relative light units (RLU) per mg of cellular proteins.

Figure 4:
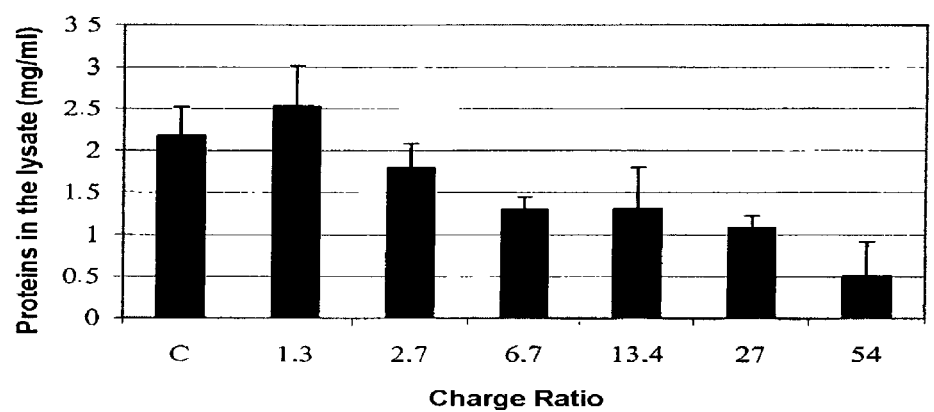

FIG. 4: Cytotoxicity of the transfecting compound KanaChol. HeLa cells were transfected in accordance with the protocol described in Example 3 using lipoplexes prepared by mixing 5 µg of plasmid DNA expressing luciferase with the amount of lipid required to form lipoplexes characterized by the charge ratio indicated. At 48 hours post-transfection, the cells were recovered and the toxicity was quantified using the total amount of cellular proteins in the cell lysate as an index of the number of cells, cell death producing a decrease in the extractable proteins. The total cellular proteins in the cell lysate is indicated as a function of the charge ratio of the lipoplexes. The data are expressed as concentration of extractable cellular proteins in the cell lysate (at fixed volume).

Figure 5:
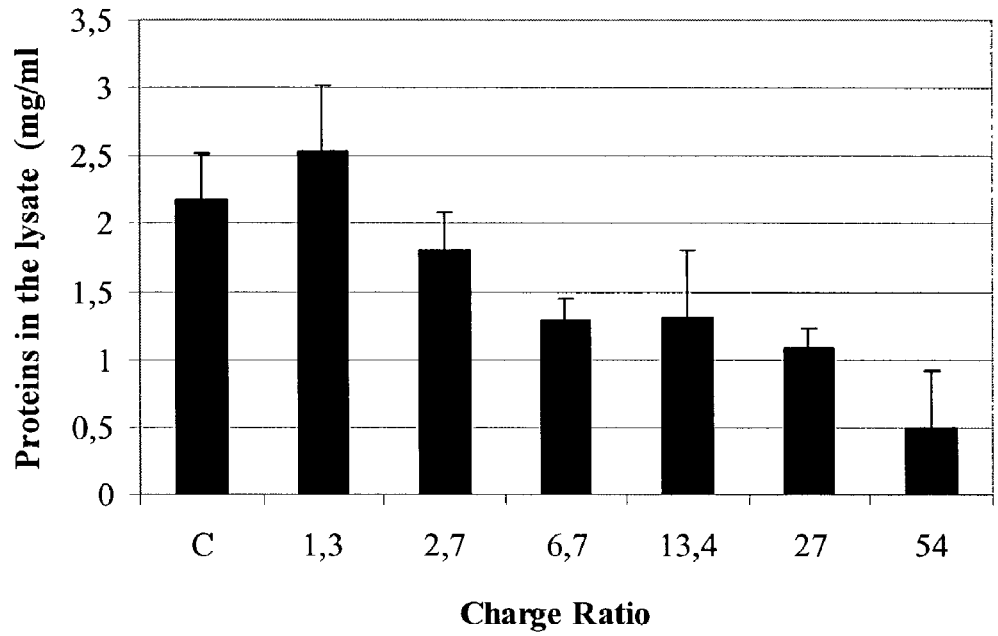

FIG. 5: Cytotoxicity of the KanaChol/DOPE (molar ratio 1:1) lipsomes. HeLa cells were transfected in accordance with the protocol described in Example 4 using lipoplexes prepared by mixing 5 µg of plasmid DNA expressing luciferase with the amount of lipid required to form lipoplexes characterized by the charge ratio indicated. At 48 hours post-transfection, the cells were recovered and the toxicity was quantified using the total amount of cellular proteins in the cell lysate as an index of the number of cells, cell death producing a decrease in the extractable proteins. The total cellular proteins in the cell lysate are indicated as a function of the charge ratio of the lipoplexes. The data are expressed as concentration of extractable cellular proteins in the cell lysate (at fixed volume).

FIG. 6: Expression of luciferase in various cell lines transfected either with the transfecting compound KanaChol or with the KanaChol/DOPE (1:1) liposomes. The various cell lines were transfected in accordance with the protocol described in Example 5 using either KanaChol/DNA lipoplexes or KanaChol/DOPE/DNA lipoplexes (with a positive charge ratio of 3-5) prepared by mixing 5 µg of plasmid DNA expressing luciferase and the required amount of lipid to obtain a positive charge ratio of 3-5. The data are expressed in relative light units (RLU) per mg of cellular proteins.

FIG. 7: Expression of luciferase in various cell lines transfected with the TGKC/DOPE (molar ratio 1:1) liposomes. The various cell lines were transfected in accordance with the protocol described in Example 6 using TGKC/DOPE/DNA lipoplexes (with a positive charge ratio of 3-5) prepared by mixing 5 µg of plasmid DNA expressing luciferase and the required amount of lipid to obtain a positive charge ratio of 3-5. The data are expressed in relative light units (RLU) per mg of cellular proteins.

FIG. 8: Transfecting activity in various cell lines (HEK293, NIH3T3, HeLa, COS, 16HBE), which were transfected with the transfecting compound NeoChol. The expression of the reporter gene can be indicated as a function of the various charge ratio of the lipoplexes and plasmid DNA. The various cell lines were transfected according to the protocol as described in Example 8, using NeoChol/DNA lipoplexes, which were prepared by mixing 5 µg of plasmid DNA expressing luciferase. The data can be expressed in relative light units (RLU) per mg of cellular proteins.

Figure 9:
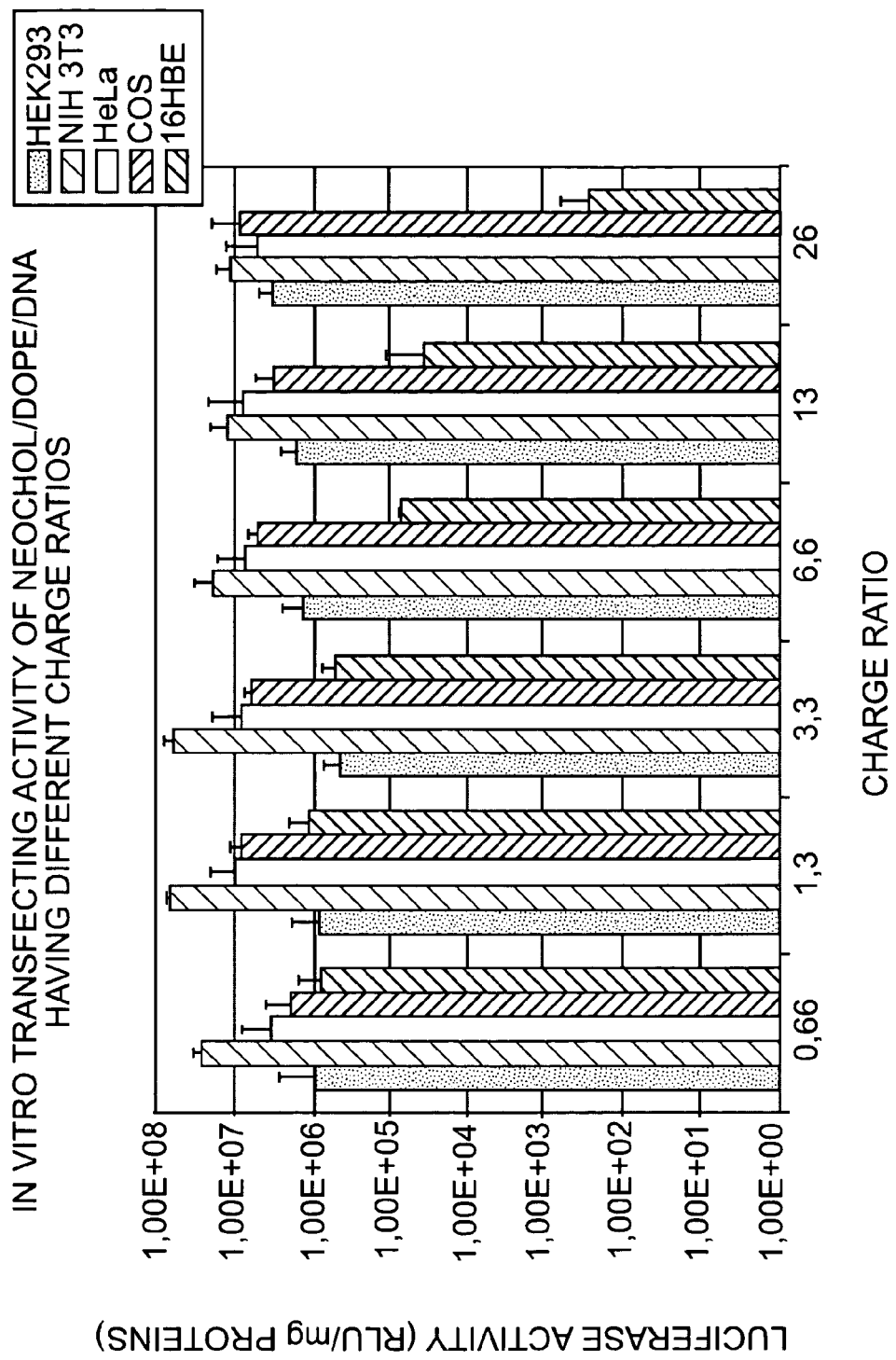

FIG. 9: Expression of luciferase in various cell lines (HEK293, NIH3T3, HeLa, COS, 16HBE), which were transfected with the transfecting compound NeoChol/DOPE (1:1). The expression of the reporter gene is indicated as a function of the various charge ratio of the lipoplexes and plasmid DNA. The various cell lines were transfected according to the protocol as described in Example 8, using NeoChol/DOPE/DNA lipoplexes, which were prepared by mixing 5 µg of plasmid DNA expressing luciferase. The data are expressed in relative light units (RLU) per mg of cellular proteins.

FIG. 10: Expression of the CAT gene in the airways of mice following instillation of KanaChol/DOPE/DNA lipoplexes stabilized with Chol-PEG (hybrid molecule for which a polyethylene glycol is covalently attached to cholesterol) or NeoChol/DOPE/DNA stabilized with Chol-PEG. These liposomes, characterized by a positive charge ratio of 3.75 for the KanaChol/DOPE/DNA stabilized with Chol-PEG, or 3.3 for the NeoChol/DOPE/DNA stabilized with Chol-PEG and a cholesterol-PEG/DNA weight/weight ratio of 2, were used to deliver a total dose of 100 µg of plasmid DNA expressing the CAT gene. Intranasal instillation was performed, and then the trachea and lungs of the mice treated were removed in order to measure the CAT expression according to the method described in Example 9. The data are expressed in ng of CAT protein/100 mg of total cellular proteins.

Figure 11:
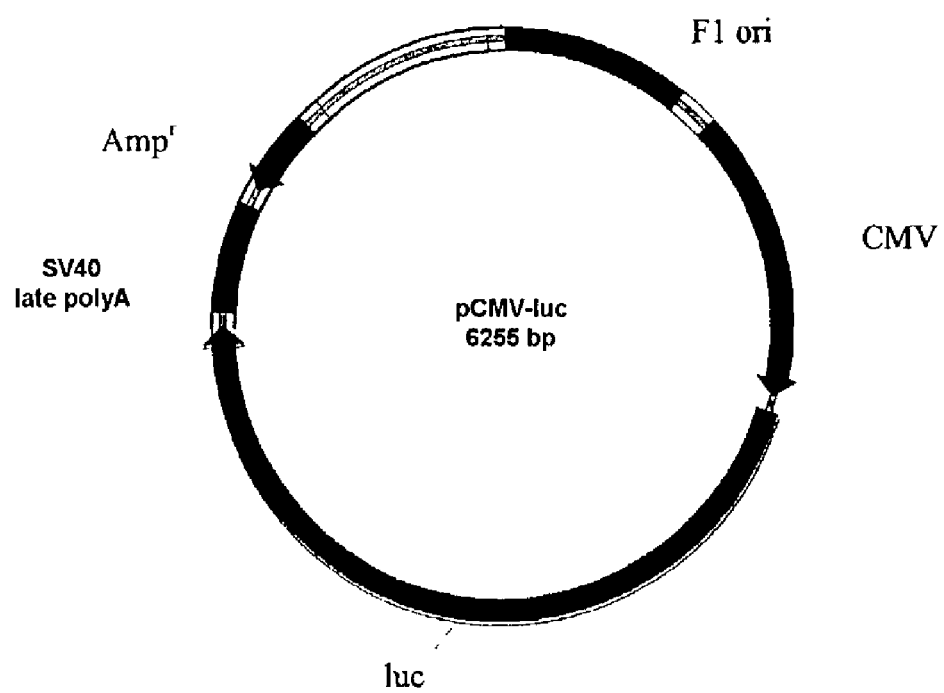

FIG. 11: Schematic representation of the plasmid pCMV-Luc.

Figure 12:
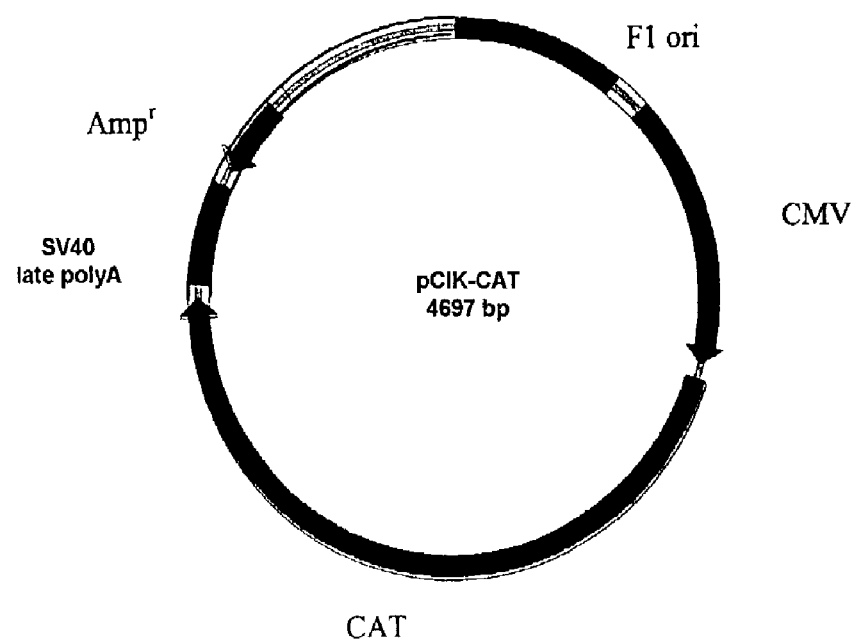

FIG. 12: Schematic representation of the plasmid pCIK-CAT.

EXAMPLES

The reagents and catalysts such as triethylamine, trifluoroacetic acid, p-toluenesulfonic acid, benzotriazol-1-yloxytripyrrolidinophosphonium hexafluorophosphate (PyBOP), dicyclohexylcarbodiimide (DCC), carbon disulfide, palladium-on-charcoal, tetradecylamine, di-tert-butyl dicarbonate, 4-dimethylaminopyridine, diisopropylethylamine, N-benzyloxycarbonyloxy-5-norbornene-2,3-dicarboximide, 2-(trimethylsilyl)ethyl p-nitrophenyl carbonate and cholesteryl chloroformiate were commercially available, as was Kanamycin A. In addition, N,N'-bis-tert-butoxycarbonylthiourea was prepared in accordance with the procedure published in *Synth. Commun.* (1993), 23, pp. 1443-1445.

The proton nuclear magnetic resonance (1H NMR) spectra were recorded on a Bruker 200 MHz spectrometer. The chemical shifts were expressed in ppm (parts per million) and the multiplicities were expressed using the usual abbreviations.

The plasmids used were:
  pCMV-Luc described in the publication by Patel et al. (BBRC, 2001, 6, pp. 536-543), which contains the luc gene encoding luciferase under the control of the CMV immediate early promoter of the cytomegalovirus. This plasmid is represented in FIG. 8. It was constructed by subcloning the CMV promoter (from the pcDNA3 plasmid of Invitrogen) upstream of the luc gene in the plasmid pGL2-Basic (Promega). It is 6255 bp in size.

pCIK-CAT (for the transfections in vivo) obtained from D. Giel (Oxford, UK), which is described by Pitard et al. (J. Med. Chem., in press). It was constructed by subcloning the E. coli CAT gene in the plasmid pCI (Promega). This plasmid is represented in FIG. 9. It is 4697 bp in size.

Example 1

Synthesis of 3β [6'-kanamycin-carbamoyl]cholesterol ("KanaChol")

a) Synthesis of [(1,3,3"-triamino)-6'-N-(benzyloxycarbonyl)]kanamycin A

N-Benzyloxycarbonyloxy-5-norbornene-2,3-dicarboximide (5.18 g; 16.5 mmol) and triethylamine (1.67 g; 16.5 mmol) were added to a solution of kanamycin A in the form of free base (8 g; 16.5 mmol) in a mixture of dimethyl sulfoxide (800 ml) and water (80 ml). After stirring overnight at room temperature, a considerable precipitate formed and analysis of the reaction mixture by TLC (thin-layer chromatography) revealed the presence of unreacted products. Water (640 ml) was then added again until the mixture became homogeneous, followed by N-benzyloxycarbonyloxy-5-norbornene-2,3-dicarboximide (2.6 g; 8.3 mmol). After 4 days of stirring, the solvents were evaporated off under vacuum and the residue was chromatographed on a silica column with an eluent ranging from a dichloromethane/methanol/ammonia (5/4/1) mixture to a methanol/ammonia (9/1) mixture. By evaporating off the solvents from the fractions concerned, the expected compound was recovered (7.15 g; 70%).

b) Synthesis of [(1,3,3"-triaza-(trimethylsilylethoxycarbonyl)]-[6'-N-(benzyloxycarbonyl)]kanamycin A ("Kana-tri[Teoc]-mono[Cbz]")

Triethylamine (0.25 g; 3 equivalents; 2.42 mmol) and mixed 2-(trimethylsilyl)ethyl p-nitrophenyl carbonate (0.92 g; 4 equivalents; 3.23 mmol) were added to a solution of Kana-mono[Cbz] (0.5 g; 0.81 mmol) in a water (7 ml)/dioxane (16 ml) mixture. The mixture was stirred at 55° C. for 48 hours and, after having been concentrated, the suspension obtained was poured into butanol presaturated with water (60 ml). After several washes with a 1N sodium hydroxide solution (800 ml) and with a saturated sodium chloride solution, the butanolic phase was evaporated to dryness. The desired product was obtained in the form of a yellow powder (0.73 g; 86%) by adding a mixture of methanol and acetone to the residue and concentrating the solution thus obtained.

c) Synthesis of [(1,3,3"-triaza(trimethylsilylethoxycarbonyl)]kanamycin A ("Kana-tri[Teoc]-NH$_2$")

Palladium-on-charcoal (Pd/C at 10%; 0.3 g) was added to a degassed solution of Kana-tri[Teoc]-mono[Cbz] (0.3 g; 0.29 mmol) in methanol (25 ml) and a stream of hydrogen was bubbled into the mixture for 1 hour. The latter was again stirred overnight under a hydrogen atmosphere, and the suspension was then filtered over celite and evaporated to dryness. The desired product in the form of a white solid (0.23 g; 90%) was thus obtained.

d) Synthesis of [(1,3,3"-triaza(trimethylsilylethoxycarbonyl)]-[6'-N-(3-oxocarbonylcholesteryl)]kanamycin A ("Kana-tri[Teoc]-Chol")

Triethylamine (1.5 equivalents; 0.017 g; 0.16 mmol) and cholesteryl chloroformiate (1.5 equivalents; 0.074 g; 0.16 mmol) were added to a solution of Kana-tri[Teoc]-NH$_2$ (0.1 g; 0.11 mmol) in a mixture of tetrahydrofuran (5 ml) and dimethylformamide (2 ml). The mixture was stirred at room temperature for 48 hours before being concentrated under reduced pressure until only the dimethylformamide remains. Adding water to this solution caused a white precipitate to form, which was filtered (0.12 g; 83%).

e) Synthesis of 1,3,3"-triamino-6'-N-(3-oxocarbonylcholesteryl)kanamycin A trifluoroacetate ("Kanachol")

The Kana-tri[Teoc]-Chol obtained in the previous step (0.070 g; 0.053 mmol) was suspended for 45 minutes in trifluoroacetic acid maintained at 0° C. in an ice bath. After having been returned to room temperature, the mixture was concentrated to dryness. The residue was taken up in methanol and again concentrated to dryness. By repeating this procedure several times, the Kanachol was obtained in the form of a white solid (0.063 g; 97%). $^1$H NMR (CD$_3$OD): δ (ppm) 5.32 (m, 1H, anomeric H); 5.09 (m, 1H, H of cholesterol); 4.97 (m, 1H, anomeric H); 4.30 (m, 1H, H of cholesterol); 3.85-2.98 (m, 16H, diverse protons of the glycosidic rings); 2.30-0.81 (m, 44H, diverse protons of the glycosidic rings and of the cholesterol nucleus); 0.63 (s, 3H, CH$_3$ of cholesterol).

Example 2

Synthesis of 3β [6'-(1,3,3"-triguanidino)kanamycin-carbamoyl]cholesterol ("TGKC")

a) Synthesis of [1,3,3"-triaza(N,N'-bis-tert-butoxycarbonyidiaminomethylene)-6'-N-(3-oxocarbonylcholesteryl)kanamycin A ("Kana-tri[GuanBoc]-Chol")

Triethylamine (30 equivalents; 0.36 g; 3.63 mmol), N,N'-bis-tert-butoxycarbonylthiourea (3.5 equivalents; 0.117 g; 0.42 mmol) and mercuric chloride (3.5 equivalents; 0.115 g; 0.42 mmol) were added successively to a solution of Kanachol, obtained according to the protocol of the above Example (0.15 g; 0.12 mmol), in dimethylformamide (10 ml). The mixture was stirred at room temperature and under an inert atmosphere for 48 hours. The solution was then poured into a mixture of water and ethyl acetate and the aqueous phase was extracted 4 times with ethyl acetate. After washing with a saturated sodium chloride solution and drying over sodium sulfate, the pooled organic fractions were concentrated to dryness. The desired product was obtained in the form of a white powder (0.1 g; 51%).

b) Synthesis of the triflate salt of [1,3,3"-triaza(N,N'-bisdiaminomethylene)-[6'-N-(3-oxocarbonylcholesteryl)kanamycin A ("Kana-tri[Guan]-Chol" or "KTGC")

The Kana-tri[GuanBoc]-Chol obtained in the previous step (0.060 g; 0.037 mmol) was suspended in trifluoroacetic acid maintained in an ice bath. After 2.5 hours at 0° C. and then returned to room temperature, the mixture was concentrated to dryness. The red-brown residue was taken up in methanol and then again concentrated to dryness. This operation was repeated 3 times. Pentane was then added and the mixture was subjected to sonication so as to obtain a fine suspension, which was then centrifuged. 0.030 g of pure KTGC was thus recovered (yield: 60%).

$^1$H NMR ($D_2O$): δ (ppm) 5.48 (m, 1H, anomeric H); 5.05 (m, 1H); 3.97 (m, 1H, H of cholesterol); 3.70-2.60 (m, diverse protons of the glycosidic rings); 2.18-0.80 (m, diverse protons of the glycosidic rings and of the cholesterol nucleus).

Example 3

Synthesis of (5"-aminoethylsulfanyl) neomycin carbamoyl cholesterol ("NeoChol")

The grafting of the aminoglycoside Neomycin to the Y-L was done by using the amino function resulting from a modification performed according to Tor et al. (*J. Am. Chem. Soc.*, 2000, 122, 980-981). Schematic reactions of the synthesis of NeoChol are represented in FIG. 1.

a) Synthesis of N-hexaterbutyloxycarbonyl NeoChol

Triethylamine (14 ml; 0.10 mmol; 1.2 equivalent) and cholesteryl chloroformiate (43.1 mg; 0.10 mmol; 1.2 equivalent) were added to a solution of amino neomycin (102 g; 0.08 mmol; 1 equivalent) which was prepared according to Tor et al. (*J. Am. Chem. Soc.*, 2000, 122, 980-981) in a mixture of tetrahydrofuranne (6 ml) and dimethylformamid (2 ml). After stirring overnight, the mixture became less clear. Volatile solvents were evaporated off under vacuum and the residue was chromatographed on a silica column with an eluent ranging from a dichloromethane/methanol/ethyl acetate 90/5/5 mixture. By evaporating off the solvents from the fractions concerned, the expected compound was recovered under the form of a white solid.

Rf=0.45 (dichloromethane/methanol 9/1)

NMR $^1$H (200 MHz, $CDCl_3$): δ (ppm) 6.15 (s widened); 5.90 (m, 1H); 5.35 (m, 2H); 5.36 (m, 1H, Chol); 5.25-4.76 (m, 5H); 4.60-3.20 (m, 15H); 3.10 (m, 1H); 2.86 (m, 2H); 2.69 (m, 2H); 2.50-1.72 (m, 10H); 1.72-0.84 (m, 87H); 0.71 (s, 3H, $CH_3$ Chol).

Mass (MALDI-TOF): [MNa$^+$] 1708.98.

b) Synthesis of the (5"-aminoethylsulfanyl)neomycin carbamoyl cholesterol trifluoroacetate The N-hexa terbutyloxycarbonyl NeoChol obtained in the previous step (60 mg; 0.035 mmol; 1 equivalent) was suspended in trifluoroacetic acid (2 ml) maintained at 0° C. in an ice bath. After 50 minutes at 0° C., the mixture was concentrated to dryness. The residue was taken up in methanol and again concentrated to dryness. After having repeated this operation three times, the solid residue was dissolved in water and lyophilized. The NeoChol was then recovered in the form of a white powder (59.6 mg; 95.2%).

NMR $^1$H (200 MHz, [$D_4$]methanol): δ6.05 (s widened, 1H); 5.46-5.31 (m, 3H); 4.43-4.29 (m, 4H); 4.21-3.82 (m, 5H); 3.67-3.11 (m, 13H); 2.89-2.60 (m, 3H); 2.58-2.25 (m, 3H); 2.20-1.73 (m, 7H); 1.72-0.84 (m, 33H); 0.71 (s, 3H, $CH_3$Chol).

Mass (MALDI-TOF): [MH$^+$] 1086.83; [MNa$^+$] 1108.80.

Example 4

Dose-response Curves of the in vitro Transfection of the Transfecting Compound KanaChol in Aqueous Medium The aim of this Example is to illustrate the ability of the transfecting compounds according to the invention to transfect cells in vitro.

This study was carried out for lipoplexes comprising various amounts of KanaChol: 6.6, 13.2, 33, 66 or 132 nmol of KanaChol per 5 μg of DNA. In order to determine the theoretical mean charge ratio, it was considered that 1 μg of DNA represents 3 nmol of negative charges and that 3 amine groups of kanamycin are protonated at neutral pH during the formation of the lipoplexes and the transfection. In fact, electrophoretic gel shift studies for the kanamycin complexed with nucleic acids suggest that the mean positive charge of the KanaChol was 2-3.

Preparation of the KanaChol/DNA lipoplexes: the KanaChol obtained according to Example 1 was dissolved in a 20 mM Hepes buffer solution (pH 7.4) at a positive charge concentration of 20 mM (considering that 3 amine functions are protonated at neutral pH). The lipoplexes were then prepared in accordance with the protocol described by Vigneron et al. (*PNAS*, 93, pp. 9682-9686, September. 1996) or by Patel et al. (*Biochem. and Biophys. Res. Comm.*, 281, pp. 536-543, 2001).

Cell culture: HeLa cells (American Type Culture Collection (ATCC) Rockville, Md., USA) derived from a human cervical epithelium carcinoma were cultured in the presence of a medium of the MEM (minimum essential medium) type supplemented with 10% of fetal calf serum and antibiotics. The medium and the additives came from Gibco/BRL Life Technologies (Gaithersburg, Md., USA). The cells were cultured in flasks at 37° C. and at 5% of carbon dioxide in an incubator. The same procedure was used for the HEK293 and COS cells.

Transfection: one day before transfection, the HeLa cells were transferred into 6-well plates with approximately 250,000 cells per well. These dilutions represent approximately 80% confluencing after 24 hours. For the transfection, the cells were washed twice and incubated at 37° C. with 500 μl of medium without serum. 500 μl of complexes containing 5 μg of plasmid DNA were added to each well (the complexes were prepared at least 30 minutes before being added to the wells).

After six hours at 37° C., the plates without serum were supplemented with 10% (v/v) of FCS ("Fetal Calf Serum").

All of the plates were placed at 37° C. and at 5% of carbon dioxide for 24 hours.

This protocol was similar to those described by Vigneron et al. (*PNAS*, 93, pp. 9682-9686, September 1996) or by Patel et al. (*Biochem. and Biophys. Res. Comm.*, 281, pp. 536-543, 2001).

Determination of luciferase activity: Briefly, the transfected cells were washed twice with 500 μl of PBS (phosphate buffer) and then lysed with 250 μl of reagent (25 mM triphosphate, pH 7.8/8 mM $MgCl_2$/1 mM dithiothreitol/15% glycerol/1% triton X-100). The lysate was then clarified by centrifugation (15 minutes at 15° C.) in a microcentrifuge.

A 20 μl aliquot of supernatant of the centrifuged lysate was diluted in 100 μl of lysis buffer, to which 4 μl of 25 mM ATP (Sigma) and 20 μl of 25 mM luciferin (Sigma) were added. The samples were then placed in a Lumet LB9501 luminometer (Berthold, Nashua, N.H.) and the light emission integration value was measured for 10 seconds.

The luciferase activity was thus expressed in Relative Light Units ("RLU") and standardized with the sample protein concentration obtained using a Biorad kit.

This protocol was similar to that described by Vigneron et al. (*PNAS*, 93, pp. 9682-9686, September 1996) or by Patel et al. (*Biochem. and Biophys. Res. Comm.*, 281, pp. 536-543, 2001).

The results for the 3 cell lines summarized in FIG. 1 show high expression levels with optimum transfection efficiency for the lipoplexes which have a theoretical mean charge ratio of approximately 5. The transfection was highest in the COS cell line.

A control was also carried out with complexes formed between kanamycin (not attached to a cholesterol derivative) and the DNA: no transfection was observed.

These data therefore demonstrate that the KanaChol makes it possible to carry out efficient transfection of DNA into cells in vitro. These results are also coherent with the hypothesis that the transfection is related to the electrostatic interaction between the positive lipoplexes and the cell surface, which is negative overall.

FIG. 2 also shows that the transfection efficiency decreases for very high charge ratios (greater than approximately 7). This decrease may reflect a certain toxic effect of cationic lipids in general, and therefore of the KanaChol in particular, when they are used in large amounts.

Thus, the cytotoxicity of the KanaChol was also measured at various charge ratios with the DNA. The toxicity was quantified using the total amount of cellular proteins in the cell lysate per well as an index of the number of cells. A decrease in the total amount of cellular proteins in the cell lysate per well corresponded to a decrease in the number of cells and, consequently, reflects the existence of a certain toxicity of the KanaChol/DNA lipoplexes with respect to the cells.

Determination of the protein level: the protein level was determined using the Biorad kit according to a protocol identical to that described by Oudrhriri et al. (*PNAS*, 94, pp. 1651-1656, 1997), and in accordance with the manufacturer's instructions.

The results summarized in FIG. 4 show a decrease in the total number of extractable cellular proteins at high charge ratio, i.e., an increase in the cytotoxicity in parallel with the increase in the KanaChol concentrations. Thus, the decrease in the transfection activity at high charge ratios in the 3 cell lines tested may be related to the existence of a certain toxicity of the KanaChol used in very large amounts.

Example 5

Dose-response Curves of the in vitro Transfection of the KanaChol/DOPE Liposomes The aim of this Example is to illustrate the ability of the transfecting compounds according to the invention to transfect cells in vitro, when they are formulated in the form of liposomes with neutral lipids.

Cationic lipids are often formulated in the form of liposomes with neutral lipid DOPE. It is in fact thought that the use of DOPE, due to its fusogenic properties, would aid transfection by facilitating the exit of the lipoplexes from the endocytic vesicles in which they are internalized. It has thus been shown by Felgner et al. (*J. Biol. Chem.*, 1994, 269, pp. 2550-2561), for a series of cationic lipids, that formulating them with 50% of DOPE makes it possible to increase the transfection efficiency 2- to 5-fold compared to formulations without zwitterionic lipid.

For this reason, KanaChol/DOPE (1:1 molar) liposomes were prepared in the following way: a mixture of KanaChol and DOPE (molar ratio 1:1) in chloroform was evaporated under vacuum and resuspended in a 20 mM Hepes buffer solution (pH 7.4). The final concentration of lipids was 5 mg/ml. The mixture was then sonicated for 10 minutes using a Branson Sonifier 450 ultrasound machine equipped with a Sonifier Cell Disruptor B-30 terminal, so as to obtain liposomes. The resulting solution was cooled to room temperature before filtration through a 0.22 µm filter (Millex G S, Millipore).

In the same way as the above Example, this study was carried out for liposomes comprising various amounts of KanaChol, so as to measure the transfection efficiency at variable theoretical mean charge ratios, in the 3 cell lines HeLa, HEK293 and COS.

The results summarized in FIG. 3 show high levels of luciferase expression for the 3 cell lines. These transfection levels are entirely comparable with those obtained with the formulations of KanaChol alone (without DOPE), which may be explained by the fact that the 3 cell lines used are very easily transfectable. On the other hand, it is observed that there is no clear decrease in the transfection activity at high charge ratios when KanaChol/DOPE/DNA liposomes are used.

Thus, the cytotoxicity of the KanaChol/DOPE liposomes was also measured at various charge ratios with the DNA, according to a protocol similar to that described in the above Example. The data summarized in FIG. 5 indicate that these liposomal formulations show no apparent toxicity at high charge ratios. It therefore appears that the KanaChol, used in liposomal formulation, is a transfection vector which is both efficient and nontoxic.

Example 6

Spectra for the in vitro Transfection Activity of the Transfecting Compound KanaChol and of the KanaChol/DOPE Liposomes The aim of this Example is to illustrate the ability of the transfecting compounds according to the invention to transfect other cell types in vitro, whether they are used alone or in the form of a liposome with DOPE.

The in vitro transfection experiments carried out in Examples 4 and 5 were again carried out in a similar way, but with other less conventional cell lines (species and specificity of each cell line are indicated in FIG. 6). The KanaChol/DNA and KanaChol/DOPE/DNA formulations were used at charge ratios of between 3 and 5 (optimum values as defined in Examples 4 and 5). The results obtained are summarized in the table of FIG. 6.

It appears that the KanaChol/DOPE (molar ratio 1:1) formulation induces high transfection efficiency for all the cell lines, the KanaChol used alone (without DOPE) being less efficient overall, in particular in the cell lines 16HBE and HepG2. It therefore appears that the use of DOPE would have a beneficial effect on transfection efficiency.

Example 7

In vitro Transfection Activity of the TGKC/DOPE Liposomes

The aim of this Example is to illustrate the ability of the polyguanidylated transfecting compounds according to the invention (formulated in the form of liposomes) to transfect cells in vitro.

TGKC/DOPE (molar ratio 1:1) formulations obtained in a similar way to the protocol described in Example 5 were thus used to transfect various cell lines (COS, HeLa, NIH3T3 and MITC) in vitro, according to transfection methods similar to those described in the previous Examples. The charge ratio of the TGKC/DOPE/DNA lipoplexes was fixed between 3 and 5, i.e., at values which had previously proved to be optimal with the KanaChol. Naturally, in order to determine the theoretical mean charge ratio, it was considered that the 3 guanidinium groups of the TGKC are positively charged at neutral pH (due to the high pKa of guanidinium functions).

The results summarized in FIG. 7 clearly show that the TGKC/DOPE liposomes make it possible to efficiently transfect the various cell lines tested.

Example 8

Spectra for the in vitro Transfection Activity of the Transfecting Compound NeoChol and of the NeoChol/DOPE Liposomes The aim of this Example is to illustrate the ability of the transfecting compounds according to the invention to transfect various cell types in vitro, whether they are used alone or in the form of a liposome with DOPE.

The in vitro transfection experiments carried out in Examples 4, 5, 6, and 7 were carried out in similar way using the NeoChol/DNA and NeoChol/DOPE/DNA formulations at various charge ratio (comprised between 1.3 and 26 for the NeoChol/DNA and between 0.66 and 26 for the NeoChol/DOPE/DNA) and with 5 different cell lines (HeLa; NIH 3T3; HEK298; COS; and 16HBE). Lipoplexes and liposomes were prepared in a similar way as described in Examples 4 and 5 (assuming that 5 amino functions are positively charged for the NeoChol at a neutral pH). The results obtained are summarized in FIGS. 8 and 9.

Results as summarized in FIG. 8 clearly show that Neo-Chol/DNA formulations permit efficient transfection of the various cell lines.

It appears that the NeoChol/DOPE formulation (1:1) includes a high efficacy of transfection for all cell lines. When used alone (without DOPE), NeoChol seems to be somewhat less efficient, particularly in cell line 16HBE (except for the high ratio charge). It thus appears that the use of DOPE has a beneficial effect on the transfection efficacy.

Example 9

In vivo Gene Transfer into the Airways of Mice Using the KanaChol/DOPE/Chol-PEG Liposomes and NeoChol/DOPE/Chol-PEG This Example illustrates the ability of the transfecting compounds according to the invention to transfect DNA into cells in vivo.

The in vivo gene transfer was carried out with 50 μl of KanaChol/DOPE/DNA or NeoChol/DOPE/DNA lipoplexes stabilized with Chol-PEG, in the airways of female BALB/c mice weighing 30 g (intranasal administration). Each animal received 3 doses, approximately 4 hours apart, i.e., a total amount of 100 μg of pCIK-CAT plasmid DNA.

The formulations used were prepared in the following way: KanaChol/DOPE liposomes were prepared according to the protocol described in Example 6. A solution of steric stabilizer Chol-PEG (a cholesterol attached to a polyethylene glycol chain containing approximately 100 oxyethylene units) was then added immediately before mixing with the pCIK-CAT plasmid DNA in aqueous solution. The DNA concentration was thus approximately 0.6 mg/ml and the positive charge ratio was 3.75. The final Chol-PEG/DNA ratio was then 2 (weight/weight). The use of Chol-PEG allowed the production of colloidally stable solutions which made it possible to have very high transfection efficiency in the airways of mice in vivo via intranasal instillation of the liposomal formulations. NeoChol/DOPE/Chol-PEG formulations were prepared in a similar way, but the positive charge ratio was then 3.3.

The reporter gene used in the present case is the CAT ("*Escherichia Coli* chloramphenicol acetyltransferase") gene. The administration into the airways was carried out by intranasal instillation. 48 hours post-transfection, the animals were killed and the lungs and trachea were removed separately for analysis. The tissue pieces were placed in a TEN buffer (40 mM of Tris-HCl, 1 mM of EDTA and 150 mM of sodium chloride, pH 7.8) and agitated on ice for approximately 30 seconds using an Ultra-Turrax T25 agitator (Fisher Bioblock Scientific, Strasbourg, France). The cells were then lysed with 3 freezing-thawing cycles and a clear supernatant was obtained by centrifugation. The CAT concentration was determined using a CAT ELISA assay carried out in accordance with the manufacturer's (Boehringer Mannheim) instructions. The CAT levels were expressed in ng of CAT protein per 100 mg of total proteins, the protein concentration being determined using a Bio-Rad assay.

The table of FIG. 10 shows the levels of expression of the CAT gene obtained in the homogenates of trachea and of lung. The expression of the CAT gene is highest in the lung. FIG. 10 also indicates that very low levels of expression were obtained after administration of identical doses of "naked" DNA (i.e. nonformulated DNA). These results suggest that, under the conditions of the experiment, the KanaChol/DOPE or NeoChol/DOPE liposomes allow a transfection efficiency in vivo, in airways of mice, which is greater than that obtained with naked DNA. The levels of expression obtained when using NeoChol/DOPE liposomes are of the same range than those that are obtained when using KanaChol/DOPE. These results are also entirely similar to those which had been obtained with BGTC/DOPE formulations (described in application WO 97/31935), these being formulations which had proved to be most particularly efficient and advantageous for transfecting airways (Densmore et al., *J. of Gene Med.*, 1999, Vol 1(4)).

The invention claimed is:

1. A transfecting compound of general formula (I):

A-Y-L (I)

in which:
A represents an aminoglycoside selected from the group consisting of kanamycin, paromomycin, and neomycin,
Y represents a spacer comprising at least one chemical function selected from ketone functions and amide functions, and
L represents:
either a radical —($R_1$)$R_2$, wherein $R_1$ and $R_2$ represent, independently of one another, a fatty aliphatic chain chosen from linear alkyl radicals containing 16, 18, 20, or 22 carbon atoms and 1 unsaturation,
or a radical —N—$R_3$ or —O—$R_3$, wherein $R_3$ represents a polycyclic cholestane compound,
or an isomer thereof, a mixture thereof, or a salt thereof.

2. The transfecting compound according to claim 1, wherein said spacer is chosen from radicals of formula:

—C(O)—; and

—W—($CH_2$)$_k$—W'—; and in which k is an integer chosen between 1 and 6 inclusive, and W and W' are groups, which may be identical or different, chosen from ketone functions and amide functions.

3. The transfecting compound according to claim 1, wherein said polycyclic cholestane compound is chosen from cholesterol, cholestanol, 3-α-cyclo-5-α-cholestan-6-β-ol, cholic acid, cholesteryl formiate, cholestanyl formiate, 3-α-5-cyclo-5-α-cholestan-6-β-yl formiate, cholesterylamine, 6-(1,5-dimethylhexyl)-3a,5a-dimethylhexadecahydrocyclopenta[a]cyclopropa[2,3]cyclopenta[1,2-f] naphthalen-10-ylamine, and cholestanylamine.

4. A transfecting compound 3β[6'-kanamycin-carbamoyl] cholesterol.

5. The transfecting compound according to claim 1, wherein the transfecting compound is (5" aminoethylsulfanyl) neomycin carbamoylcholesterol.

6. A composition comprising a transfecting compound according to claim 1, and a nucleic acid.

7. The composition according to claim 6, wherein the nucleic acid is a deoxyribonucleic acid or a ribonucleic acid.

8. The composition according to claim 6, wherein said nucleic acid comprises at least one gene of therapeutic interest under the control of a regulatory sequence.

9. The composition according to claim 6, wherein said nucleic acid is an antisense sequence or gene.

10. The composition according to claim 6, further comprising at least one adjuvant.

11. The composition according to claim 10, wherein the at least one adjuvant is at least one of a lipid, peptide, protein, and polymer.

12. The composition according to claim 11, wherein said at least one adjuvant is chosen from neutral lipids.

13. The composition according to claim 12, wherein said neutral lipid is chosen from natural and synthetic lipids which are zwitterionic or lack ionic charge under physiological conditions.

14. The composition according to claim 13, wherein said neutral lipid is chosen from dioleoylphosphatidylethanolamine, oleoyl-palmitoylphosphatidylethanolamine, distearoyl-, dipalmitoyl- and dimirystoylphosphatidylethanolamines and derivatives thereof that are N-methylated 1 to 3 times, phosphatidylglycerols, diacylglycerols, glycosyldiacylglycerols, cerebrosides, sphingolipids, asialogangliosides, dioleoylphosphatidylcholine, and cholesterol.

15. The composition according to claim 14, wherein said cerebrosides comprise a galactocerebroside.

16. The composition according to claim 14, wherein said sphingolipids comprise a sphingomyelin.

17. The composition according to claim 14, wherein said asialogangliosides comprise at least one of asialoGM1 and asialoGM2.

18. The composition according to claim 11, wherein said at least one adjuvant is polyethylene glycol or polyethylene glycol-cholesterol.

19. The composition according to claim 6, further comprising an extracellular or intracellular targeting element.

20. The composition according to claim 19, wherein said targeting element is chosen from sugars, peptides, proteins, oligonucleotides, lipids, neuromediators, hormones, vitamins, and derivatives thereof.

21. The composition according to claim 19, wherein said targeting element is covalently attached to a fatty alkyl chain containing at least 10 carbon atoms or to a polyethylene glycol.

22. The composition according to claim 19, wherein said targeting element is covalently attached either to the transfecting compound, or to the nucleic acid.

23. The composition according to claim 6, further comprising a vehicle that is pharmaceutically acceptable for an injectable formulation.

24. The composition according to claim 6, further comprising a vehicle that is pharmaceutically acceptable for administration on the skin and/or mucous membranes.

25. A method for transferring a nucleic acid into cells, comprising:
(1) bringing the nucleic acid into contact with a transfecting compound of claim 1, so as to form a complex, and
(2) bringing the cells into contact with the complex formed in (1).

26. The transfecting compound according to claim 1, wherein the spacer Y is chosen from —C(O)— and —W—$(CH_2)_k$—W'-; wherein k is an integer chosen between 1 and 6 inclusive, and W and W' are groups, which may be identical or different, chosen from —C(O)— and —N(H)—C(O)—.

27. The transfecting compound according to claim 1, wherein the spacer Y is —C(O)—N(H)—$(CH_2)_2$—S—.

28. A transfecting compound of general formula (I):

in which:
A represents an aminoglycoside selected from the group consisting of kanamycin, paromomycin, and neomycin;
Y represents a spacer chosen from —C(O)—, —C(O)—N(H)—$(CH_2)_2$—S—, and —W—$(CH_2)_k$—W'-;
wherein k is an integer chosen between 1 and 6 inclusive, and W and W' are groups, which may be identical or different, chosen from —C(O)— and —N(H)—C(O)—; and
L represents:
either a radical —$(R_1)R_2$, wherein $R_1$ and $R_2$ represent, independently of one another, a fatty aliphatic chain chosen from linear alkyl radicals containing 16, 18, 20, or 22 carbon atoms and 1, 2, or 3 unsaturations,
or a radical —N—$R_3$ or O—$R_3$, wherein $R_3$ represents a polycyclic cholestane compound,
or an isomer thereof, a mixture thereof, or a salt thereof.

29. A transfecting compound of general formula (I):

in which:
A represents an aminoglycoside selected from the group consisting of kanamycin, paromomycin, and neomycin;
Y represents a spacer chosen from —C(O)—, —C(O)—N(H)—$(CH_2)_2$—S—, and —W—$(CH_2)_k$—W'-;
wherein k is an integer chosen between 1 and 6 inclusive, and W and W' are groups, which may be identical or different, chosen from —C(O)— and —N(H)—C(O)—; and
L represents:
either a radical $(R_1)R_2$, wherein $R_1$ and $R_2$ represent, independently of one another, a fatty aliphatic chain chosen from saturated linear alkyl radicals containing 10 to 22 carbon atoms;
or a radical —N—$R_3$ or —O—$R_3$, wherein $R_3$ represents a polycyclic cholestane compound,
or an isomer thereof, a mixture thereof, or a salt thereof.

30. A transfecting compound according to claim 28, wherein the polycyclic cholestane compound is chosen from cholesterol, cholestanol, 3-α-5-cyclo-5-α-cholestan-6-β-ol, cholic acid, cholesteryl formiate, cholestanyl formiate, 3-α-5-cyclo-5-α-cholestan-6-yl formiate, cholesterylamine, 6-(1,5-dimethylhexyl)-3a,5a-dimethylhexadecahydrocyclopenta[a]cyclopropa[2,3]cyclopenta[1,2-f]naphthalen-10-ylamine and cholestanylaminel.

31. A transfecting compound according to claim 29, wherein the polycyclic cholestane compound is cholesterol, cholestanol, 3-α-5-cyclo-5-α-cholestan-6-β-ol, cholic acid, cholesteryl formiate, cholestanyl formiate, cyclo-5-α-cholestan-6-yl formiate, cholesterylamine, 6-(1,5-dimethylhexyl)-3a,5a-dimethylhexadecahydrocyclopenta[a]cyclopropa[2,3]cyclopenta[1,2-f]naphthalen-10-ylamine and cholestanylaminel.

* * * * *